(12) United States Patent
Suehira et al.

(10) Patent No.: US 10,582,857 B2
(45) Date of Patent: Mar. 10, 2020

(54) ULTRASONIC APPARATUS

(71) Applicant: CANON KABUSHIKI KAISHA, Tokyo (JP)

(72) Inventors: Nobuhito Suehira, Tokyo (JP); Fumitaro Masaki, Tokorozawa (JP); Kazuhiko Fukutani, Yokohama (JP); Takuro Miyasato, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 259 days.

(21) Appl. No.: 15/416,777

(22) Filed: Jan. 26, 2017

(65) Prior Publication Data
US 2017/0215737 A1    Aug. 3, 2017

(30) Foreign Application Priority Data
Jan. 29, 2016  (JP) ................... 2016-016445

(51) Int. Cl.
*A61B 5/00* (2006.01)
*A61B 8/08* (2006.01)
*A61B 8/00* (2006.01)

(52) U.S. Cl.
CPC .......... *A61B 5/0095* (2013.01); *A61B 5/0073* (2013.01); *A61B 8/0825* (2013.01);
(Continued)

(58) Field of Classification Search
CPC ... A61B 5/0095; A61B 8/0825; A61B 5/0073; A61B 8/4483; A61B 2562/14; A61B 5/4312
See application file for complete search history.

(56) References Cited

U.S. PATENT DOCUMENTS

2002/0045819 A1* 4/2002 Garlick ............... A61B 8/0825
                                                                600/437
2013/0031982 A1    2/2013 Sato
(Continued)

FOREIGN PATENT DOCUMENTS

CN    1792335 A    6/2006
CN    103492871 A    1/2014
(Continued)

OTHER PUBLICATIONS

Thomas Felix Fehm, et al. Four dimensional hybrid ultrasound and optoacoustic imaging via passive element optical excitation in a hand-held probe, Appl. Phys. Lett. 105, 173505 (2014).

*Primary Examiner* — Rex R Holmes
(74) *Attorney, Agent, or Firm* — Canon U.S.A.Inc., IP Division (57) ABSTRACT

An ultrasonic apparatus includes an ultrasonic wave generating member having a light absorbing member that generates an ultrasonic wave when irradiated by a light from a light irradiating portion, and a transducer that detects the ultrasonic wave and converts the ultrasonic wave into an electric signal. The ultrasonic wave generating member includes an area that has a different light absorption coefficient in an irradiation area irradiated by the light from the light irradiating portion. Furthermore, in an area in which the light absorbing member is disposed, when an area irradiated by the light from the light irradiating portion is referred to as a transmitted ultrasonic wave generating area, the transmitted ultrasonic wave generating area functions as a surface sound source.

18 Claims, 4 Drawing Sheets

(52) U.S. Cl.
CPC .......... *A61B 8/4483* (2013.01); *A61B 5/4312* (2013.01); *A61B 2562/14* (2013.01)

(56) References Cited

U.S. PATENT DOCUMENTS

| | | |
|---|---|---|
| 2013/0190595 A1 | 7/2013 | Oraevsky |
| 2013/0245420 A1* | 9/2013 | Fukutani .............. A61B 5/0095 600/407 |
| 2017/0065180 A1* | 3/2017 | Miyasato ............. A61B 5/0095 |

FOREIGN PATENT DOCUMENTS

| | | |
|---|---|---|
| JP | 2011-120795 A | 6/2011 |
| JP | 2014-094225 A | 5/2014 |
| WO | 2015/106188 A1 | 7/2015 |

\* cited by examiner

ULTRASONIC APPARATUS

BACKGROUND OF THE INVENTION

Field of the Invention

The present disclosure relates to an ultrasonic apparatus that acquires information of a subject using an ultrasonic wave.

Description of the Related Art

In recent years, photoacoustic tomography (PAT) has been proposed as an optical imaging technology. When a measurement light, such as a pulsed laser, is irradiated to a subject, an acoustic wave is generated while the measurement light is absorbed inside the subject. The above phenomenon is referred to as a photoacoustic effect, and the acoustic wave generated with the photoacoustic effect is referred to as photoacoustic wave.

Since the absorption coefficient of the light energy is different in the tissues constituting the subject, the generated sound pressures of the photoacoustic waves are different. In photoacoustic tomography, the generated photoacoustic wave is detected with transducers, and by analyzing the received signal, information related to the optical characteristics inside the subject can be formed into an image.

Meanwhile, ultrasonic imaging is known as a method of acquiring structural information inside the subject. In ultrasonic imaging, ultrasonic waves are transmitted to the subject from a plurality of ultrasonic wave transducers disposed in a probe, and reflected wave generated at interfaces with different acoustic impedances are received and analyzed. With the above, information (structural information) related to the sound characteristic of the subject can be formed into an image.

An apparatus that combines the above technique, in which light is irradiated to an ultrasonic wave generating member disposed external to the subject to generate a photoacoustic wave (an ultrasonic wave) is desired. In such an apparatus, the above photoacoustic wave is used to perform ultrasonic imaging. Such a technique is referred to as a photoacoustic induced ultrasonic imaging apparatus so as to distinguish the apparatus from a typical pulse-echo ultrasonic imaging that uses an ultrasonic wave electrically generated with an acoustic wave (ultrasonic wave) transmitting element as a transmission wave.

Non-patent literature "Four dimensional hybrid ultrasound and optoacoustic imaging via passive element optical excitation in a hand-held probe Appl. Phys. Lett. 105, 173505 (2014)" describes a photoacoustic induced ultrasonic imaging apparatus that uses a microsphere light absorbing member as an ultrasonic wave generating member.

In a typical pulse-echo ultrasonic imaging apparatus that includes a plurality of transducers that transmit ultrasonic waves, the intensity distribution of the ultrasonic waves irradiated to the subject can be changed optionally by changing the voltage of each transducer.

On the other hand, with the method described in the non-patent literature, the intensity distribution of the ultrasonic waves cannot be adjusted.

SUMMARY OF THE INVENTION

The present disclosure provides, in a photoacoustic induced ultrasonic imaging apparatus, an ultrasonic apparatus that is capable of generating an ultrasonic wave having a desired intensity distribution, or that is capable of making the intensity distribution of the generated ultrasonic wave close to a desired intensity distribution.

An ultrasonic apparatus of the present disclosure includes a transducer that receives an ultrasonic wave and converts the ultrasonic wave into an electric signal, a planar ultrasonic wave generating member including a light absorbing member, and a light irradiating portion that irradiates pulsed light to the ultrasonic wave generating member. In the ultrasonic apparatus, the ultrasonic wave generating member shows a distribution of light absorption characteristics in a planar direction regarding about an illuminance distribution of the pulsed light irradiated from the light irradiating portion.

Further features of the present disclosure will become apparent from the following description of exemplary embodiments with reference to the attached drawings.

DESCRIPTION OF THE EMBODIMENTS

Hereinafter, preferred embodiment of the present disclosure will be described in detail with reference to the drawings. Note that the same reference numerals will be basically attached to the same components and redundant description thereof will be omitted. The ultrasonic apparatus of the present exemplary embodiment includes an ultrasonic wave generating member having a light absorbing member that generates an ultrasonic wave when irradiated by light, and acquires information of a subject by irradiating, to the subject, an ultrasonic wave that is generated when the ultrasonic wave generating member is irradiated by light. The light absorbing member of the present exemplary embodiment generates a planar ultrasonic wave. Accordingly, compared with generation of a spherical ultrasonic wave, attenuation of the ultrasonic wave until the subject is irradiated can be suppressed to a small degree. Additionally, the ultrasonic wave generating member has an in-plane distribution of the absorption coefficient of the light irradiated to the irradiation area that is irradiated by light. With the above, an ultrasonic wave having an intensity distribution different from the intensity distribution of the light irradiated to the irradiation area can be generated. For example, when a planar ultrasonic wave having, to the extent possible, a uniform intensity is to be generated, an ultrasonic wave having an intensity fluctuation that is smaller than the irradiation fluctuation of the light can be generated by using an ultrasonic wave generating member having an absorption coefficient distribution that cancels out the irradiation fluctuation of the light.

Note that in the present disclosure and the specification, the acoustic wave generated from the light absorbing member of the subject (including both the inside and the surface) irradiated by light is referred to as a photoacoustic wave, and the electric signal obtained by converting the photoacoustic wave is referred to as a photoacoustic wave signal. Furthermore, the image obtained by reconstructing the photoacoustic wave signal is referred to as a photoacoustic image. Meanwhile, the photoacoustic wave (the ultrasonic wave) that is generated by the ultrasonic wave generating member when irradiated by light and that is transmitted to the subject is referred to as a transmitted ultrasonic wave, and the transmitted ultrasonic wave that is reflected or scattered from the subject (including both the inside and the surface) is referred to as a reflected wave. Furthermore, the electric signal obtained by converting the reflected wave is referred to as an ultrasonic wave signal, and the image obtained by reconstructing the ultrasonic wave signal is referred to as an ultrasound image.

Hereinafter, the exemplary embodiment of the present disclosure will be described in further detail.

In the present exemplary embodiment, a subject information acquisition apparatus that not only can perform the photoacoustic induced ultrasonic imaging described above but can perform photoacoustic tomography as well will be described. In the present exemplary embodiment, photoacoustic induced ultrasonic imaging is performed by receiving and converting the transmitted ultrasonic wave that has been reflected and scattered from the subject, by acquiring, on the basis of the acquired ultrasonic wave signal, acoustic characteristic value distribution information inside the subject, and by performing visualization (imaging). Note that the acoustic characteristic value distribution information generally represents sound pressure distribution, acoustic impedance difference distribution, scatter intensity distribution, sound-velocity distribution, acoustic attenuation distribution, or distribution data including the values related to the above distributions. Furthermore, in the present exemplary embodiment, photoacoustic tomography is performed by irradiating pulsed light to the subject, receiving and converting, with the transducers, the photoacoustic wave generated inside the subject induced by the pulsed light, acquiring, on the basis of the acquired photoacoustic wave signal, the information related to the optical characteristic inside the subject, and performing visualization. The information related to the optical characteristic generally represents initial sound pressure distribution inside the subject, optical absorption energy density distribution, absorption coefficient distribution, or characteristic distribution related to the concentration of substances constituting the tissue. The characteristic distribution related to the concentration includes the distribution of, for example, oxygen saturation, total hemoglobin concentration, oxyhemoglobin concentration, or deoxyhemoglobin concentration. Furthermore, the characteristic distribution related to the concentration may be the distribution of glucose concentration, collagen concentration, melanin concentration, or volume fraction of fat and water. Note that the subject information acquisition apparatus according to the embodiment of the present exemplary embodiment is a form of the ultrasonic apparatus. In the present disclosure and the present specification, any device that acquires information of the subject by generating ultrasonic wave is referred to as an ultrasonic apparatus even in a device in which photoacoustic tomography is not performed.

System Configuration

Figure 1A:
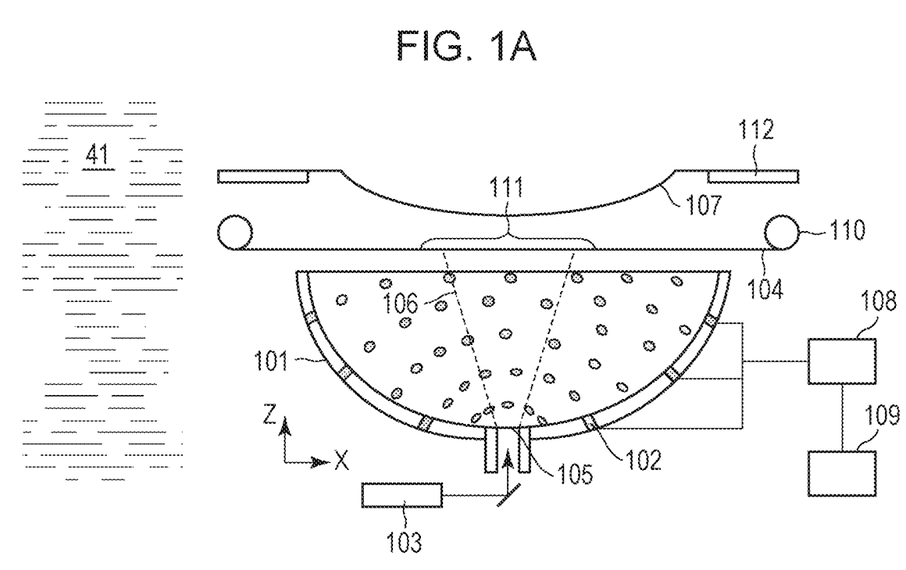
FIGS. 1A and 1B are diagrams illustrating a configuration of a photoacoustic measurement apparatus according to an exemplary embodiment.
Figure 1B:
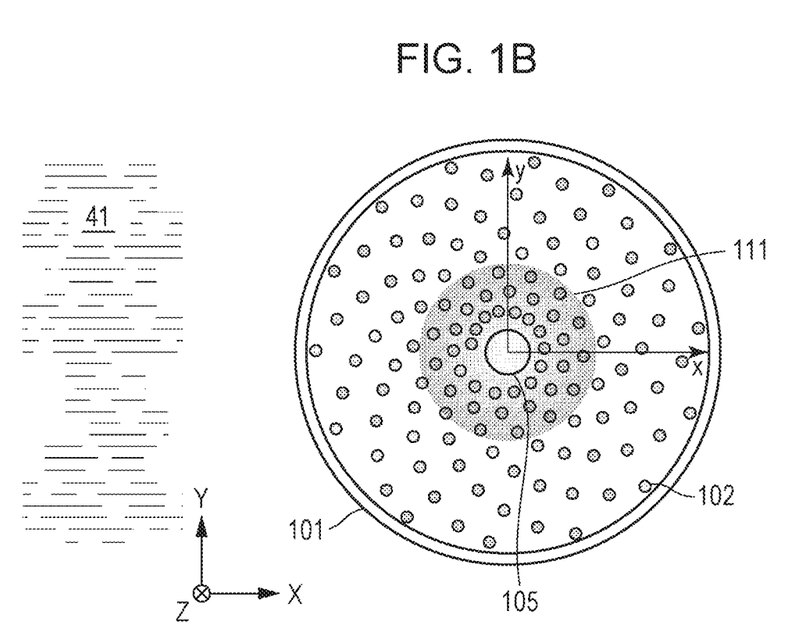

Referring to FIGS. 1A and 1B, a configuration of the subject information acquisition apparatus according to the present exemplary embodiment will be described. The subject information acquisition apparatus according to the present exemplary embodiment includes a probe unit 101 including a light source 103 and a plurality of transducers 102, an acoustic wave processing unit 108, an ultrasonic wave generating member 104, a subject holding member 107, and an apparatus control unit 109. The pulsed light emitted from the light source 103 is guided through an optical transmission line, reaches the ultrasonic wave generating member 104, and generates an ultrasonic wave. At least a portion (transmitted ultrasonic wave) of the ultrasonic wave is transmitted to the subject. The transmitted ultrasonic wave that has propagated inside the subject held by the subject holding member 107 is emitted to the ultrasonic scatterers inside the subject, is reflected and scattered, and generates a reflected wave. The reflected wave is received by the transducers 102 of the probe unit 101 and is converted into an electric signal. The electric signal is processed in the acoustic wave processing unit 108 and the apparatus control unit 109 and ultrasound image data (acoustic characteristic value distribution information data) of the subject is acquired. Note that when photoacoustic wave imaging is performed, the photoacoustic wave signal is acquired by retreating a light absorbing member 111 of the ultrasonic wave generating member 104 from the optical path between the subject and the light irradiating portion 105, and receiving and converting the photoacoustic wave, with the transducers 102, generated when the subject is irradiated by pulsed light. Furthermore, the photoacoustic image data (optical characteristic information data) of the subject is acquired by processing the photoacoustic wave signal with the acoustic wave processing unit 108 and the apparatus control unit 109. The ultrasound image data and the photoacoustic image data obtained in the above manner are tuned into an image and the image is displayed on the display device.

Hereinafter, the components of the subject information acquisition apparatus according to the present exemplary embodiment will each be described in further detail.

Probe Unit

The probe unit 101 includes the transducers 102 and is a holding unit. The subject information acquisition apparatus of the present exemplary embodiment includes the probe unit 101 having a hemispherical shape illustrated in FIGS. 1A and 1B, and the plurality of transducers 102 are disposed on the inner surface thereof. FIG. 1B is a schematic diagram of the subject information acquisition apparatus according to the present exemplary embodiment observed from above in the vertical direction (a Z-axis direction). On the probe unit 101, 512 transducers 102 are disposed along the hemispherical surface of the probe unit 101 in a spiral manner.

Furthermore, the light irradiating portion 105 is provided at a bottom portion of the probe unit 101, such that pulsed light 106 can be irradiated to the subject in the Z-axis direction.

Note that in the present exemplary embodiment, the light irradiating portion 105 is an opening, and light is emitted from an optical transmission line that transmits light from the light source 103. In other words, the light irradiating portion 105 is optically connected to the light source 103.

The probe unit 101 is capable moving along an XY plane with an XY stage (not shown). Such a configuration enables emission of pulsed light and reception of the reflected wave and the photoacoustic wave to be performed at a plurality of positions with respect to the subject, and the measurement accuracy can be improved. Note that the acoustic matching material serving as an acoustic matching layer is filled between the holding member 107 and the probe unit 101. The acoustic matching material is, for example, liquid 41 or gel, and in the present exemplary embodiment, water is used. Furthermore, the ultrasonic wave generating member 104 is capable of integrally moving with the motion of the probe unit 101. Note that the probe unit is not limited to the above configuration as long as the held transducers can receive the reflected wave and convert the reflected wave into an electric signal. For example, the probe unit may have a flat surface and the transducers may be arranged on the flat surface. Typically, a probe unit in which a plurality of transducers 102 are arranged one-dimensionally or two-dimensionally is used. Using such a multidimensional array element, the reflected wave and the photoacoustic wave can be detected simultaneously at a plurality of locations such that the detection time can be decreased and the effect of the vibration of the subject and the like can be reduced.

Transducer

The transducers 102 are members that detect the reflected wave and the photoacoustic wave arriving from the subject and that convert the reflected wave and the photoacoustic wave each into an electric signal (an ultrasonic wave signal or a photoacoustic wave signal). The transducers 102 are referred to as ultrasonic wave transducers, acoustic wave transducers, acoustic wave detectors, or transducers. Note that in the present exemplary embodiment, the transducers 102 need to detect both the reflected wave and the photoacoustic wave of the transmitted ultrasonic wave and convert them into electric signals.

The frequency of the photoacoustic wave generated from an organism ranges from 100 KHz to 100 MHz. Meanwhile, the frequency of the transmitted ultrasonic wave is determined by the thickness of the sound generating member, and is 8 MHz or under, for example. An ultrasonic wave detector that is capable of receiving the frequency band described above is used as the transducer 102. Specifically, a conversion element using piezoelectric ceramics (PZT), a conversion element using resonance of light, or an electrostatic capacitance type capacitive micromachined ultrasonic transducer (CMUT) may be used. In the present exemplary embodiment, the CMUT is used as the transducer 102. Note that the transducers 102 are, desirably, transducers that have a high sensitivity and a wide frequency band. In the present exemplary embodiment, a transducer that is a single element having an opening of 3 mm and that has a band of 0.5 to 5 MHz is used as the transducer 102. By obtaining the sensitivity in the low frequency band, dropout of a relatively thick blood vessel of about 1 to 3 mm can be prevented.

Acoustic Wave Processing Unit

The acoustic wave processing unit 108 includes an amplifier, an A/D converter, and the like and is a member that amplifies the electric signals converted by the transducers 102 and that converts the electric signals into digital signals. The signals after conversion are transmitted to the apparatus control unit 109. In the present exemplary embodiment, the sampling frequency of the acoustic wave processing unit 108 is 20 MHz, and the sampling number is 2048. Furthermore, signed 12-bit data is output.

Ultrasonic Wave Generating Member

The ultrasonic wave generating member 104 for generating the transmitted ultrasonic wave is disposed between the probe unit 101 and the subject holding member 107. The ultrasonic wave generating member 104 can be disposed in the light irradiation area with a drive mechanism 110. Note that an arm may be attached to the ultrasonic wave generating member 104, and the ultrasonic wave generating member may be disposed by the movement of the arm.

Figure 2A:
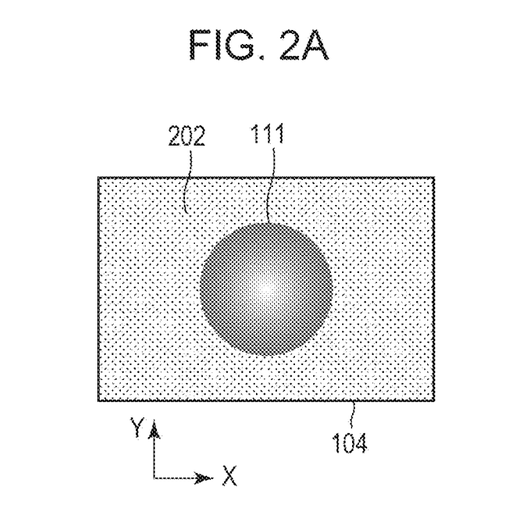
FIGS. 2A and 2B are diagrams illustrating a configuration of a sound generating member according to the exemplary embodiment.
Figure 2B:
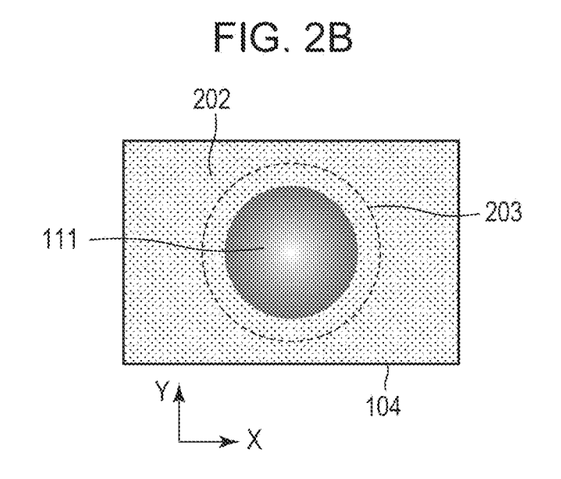

FIGS. 2A and 2B illustrate the configuration of the ultrasonic wave generating member 104. In the ultrasonic wave generating member 104, the light absorbing member 111 is disposed on a film 202 with a substantially flat surface. The film 202 is a support member of the light absorbing member 111, and in the present exemplary embodiment, the film 202 is a sheet-like support member (referred to as a sheet member). The film 202 desirably has high transmittance of ultrasonic wave (the transmitted ultrasonic wave and the reflected wave), since the generated transmitted ultrasonic wave is reflected from the subject and the reflected wave arrives at the transducers 102 again through the ultrasonic wave generating member 104. Accordingly, desirably, a material with high transmittance of ultrasonic wave, such as polyethylene terephthalate, nylon, vinyl, polycarbonate, acryl, or rubber, is used. The thickness is, desirably, thin from about 50 to 500 µm.

The light absorbing member 111 can be fabricated by coating a pigment ink, a dye ink, or a resin ink on the film 202 with an ink jet printer or the like. The material of the pigment includes a black pigment, such as a carbon black, or a cyan pigment, such as copper phthalocyanine. Furthermore, metal such as gold, silver, or aluminum may be deposited. Furthermore, a compound such as titanium oxide may be combined as scatterers. Furthermore, a light absorbing member may be applied on the film 202 and heat may be applied so that the light absorbing member is diffused inside the film. When the light absorbing member is on the surface of the film, since the layer of the light absorbing member is thin, a transmitted ultrasonic wave in a broad band region including a high frequency can be generated. Conversely, when the light absorbing member is diffused inside and the thickness of the layer of the light absorbing member is increased, the wave becomes a transmitted ultrasonic wave having a low frequency in accordance with the thickness of the layer of the light absorbing member. Note that by laminating the films, a transmitted ultrasonic wave with a lower frequency can be generated. It is only sufficient that the transmitted ultrasonic wave that is generated includes the frequency within the band that can be received by the transducers 102, and when a frequency with an unnecessary band is included, the frequency becomes a noise.

FIG. 2B illustrates an irradiation area 203 of the pulsed light 106. The area (hereinafter, referred to as a transmitted ultrasonic wave generating area) that is irradiated by the pulsed light and that actually generates the ultrasonic wave is an area in the light absorbing member 111 that is irradiated by pulsed light and is an area where the light absorbing member 111 and the irradiation area 203 overlap each other. In the case of the present exemplary embodiment, as illustrated in FIG. 2B, since the light absorbing member 111 is included inside the irradiation area 203, the entire light absorbing member 111 is the transmitted ultrasonic wave generating area.

Figure 4A:
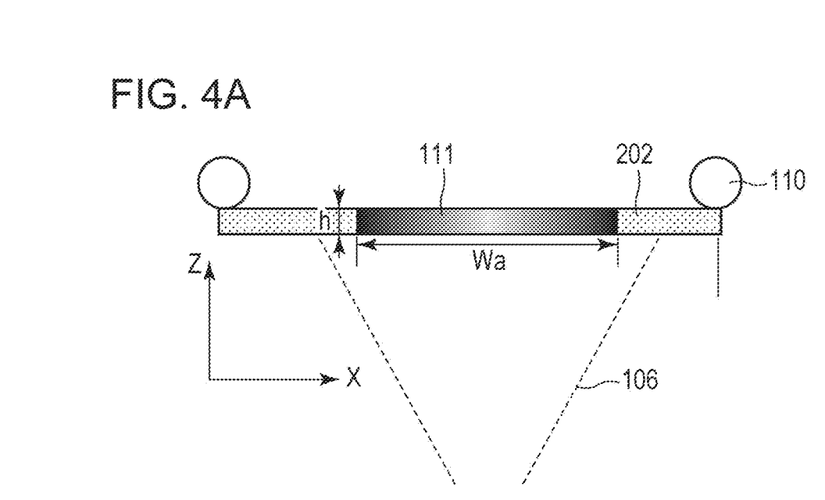
FIGS. 4A to 4C are schematic diagrams of an ultrasonic wave generating member according to variation examples.
Figure 4B:
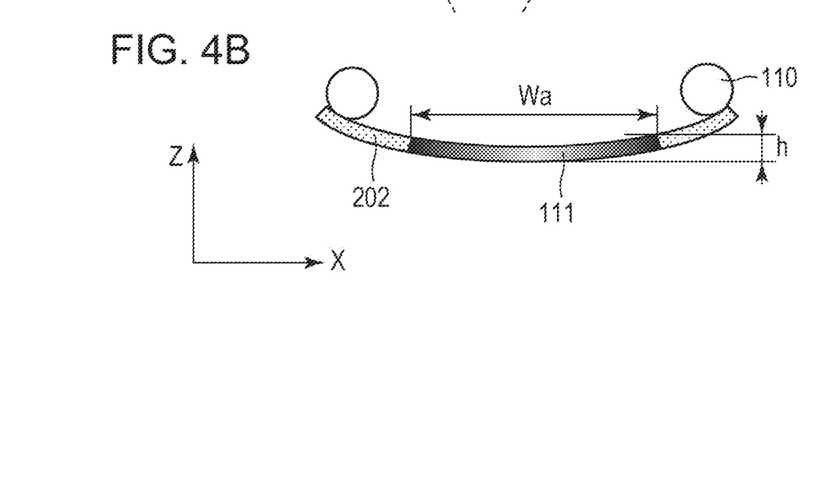

The ultrasonic wave generating member 104 of the present exemplary embodiment serves as a surface sound source. Note that the ultrasonic wave generating member functioning as the surface sound source denotes that, among the ultrasonic wave generating member, the transmitted ultrasonic wave generating area which is the area where the ultrasonic wave is actually generated functions as the surface sound source. In the present disclosure and the specification, the transmitted ultrasonic wave generating area is assumed to function as the surface sound source when a width $w_a$ of the transmitted ultrasonic wave generating area is ten times or larger than a height h. Referring to FIGS. 2B and 4A, the width $w_a$ and the height h of the transmitted ultrasonic wave generating area will be described. As illustrated in FIG. 2B, the surface of the transmitted ultrasonic wave generating area viewed from the light irradiating portion is referred to as an xy flat surface. Note that the Z-axis extends in a direction perpendicular to the drawing and corresponds to a direction in which an optical axis extends. The width $w_a$ of the transmitted ultrasonic wave generating area denotes the width in the X-axis direction and the width in the Y-axis direction, and the transmitted ultrasonic wave generating area is assumed to function as the surface sound source when both the width in the X-axis direction and the width in the Y-axis direction is ten times or larger than the height h. Note that as illustrated in FIG. 2B, in a case in which the transmitted ultrasonic wave generating area is a circle, the width $w_a$ is the diameter. Furthermore, the height h of the transmitted ultrasonic wave generating area denotes the length of the transmitted ultrasonic wave generating area in the optical axis direction (the Z-axis). More specifically, as in FIG. 4A, the height h is a length between a surface on the light irradiating portion side and a surface on the opposite side of the surface on the light irradiating portion side parallel to the Z-axis. As in the present exemplary embodiment, in a case in which the transmitted ultrasonic wave generating area is a flat surface, the height of the transmitted ultrasonic wave generating area coincides with the thickness of the light absorbing member. On the other hand, as illustrated in FIG. 4B, in a case in which the transmitted ultrasonic wave generating area has a curvature, the height h of the transmitted ultrasonic wave generating area becomes larger than the thickness of the light absorbing member; however, if the width $w_a$ is ten times or larger than the thickness h, the transmitted ultrasonic wave generating area functions as the surface sound source.

Incidentally, a method can be conceived as well that does not use the ultrasonic wave generating member 104 and another linear probe or the transducers 102 of the probe unit 101 are used to transmit the ultrasonic wave to the subject and acquire the ultrasound image. In such cases, since another linear probe is required or a function of transmitting the ultrasonic wave needs to be added to the probe unit, cost increases. Accordingly, there is an advantage in using the ultrasonic wave generating member 104. In particular, as in the present exemplary embodiment, in a case of an ultrasonic apparatus in which measurement of the photoacoustic wave is also conducted, addition of the ultrasonic wave generating member to the configuration required for measuring the photoacoustic wave enables the measurement of the ultrasonic wave to be conducted.

In-Plane Distribution of Light Absorbing Member

In the ultrasonic wave generating member 104, the light irradiation area 203 has areas that are different in the light absorption coefficient. Additionally, in the subject information acquisition apparatus of the present exemplary embodiment, the light absorbing member 111 inside the irradiation area 203 has areas that are different in the absorption coefficient. When the intensity of the light irradiated to the irradiation area 203 is not uniform, the in-plane distribution of the light absorbing member 111 in the light irradiation area 203 is, desirably, disposed such that the intensity distribution of the irradiation light is reduced. In the irradiation area 203 of the present apparatus, the beam profile of the irradiation light has a Gaussian-shaped intensity distribution. In other words, when the in-plane distribution of the absorption coefficient of the light absorbing member is uniform, the intensity distribution of the transmitted ultrasonic wave becomes a Gaussian-shaped intensity distribution.

Generation of the transmitted ultrasonic wave will be described now. A sound pressure P of the transmitted ultrasonic wave is expressed by Equation (1) in the same manner as an ordinary photoacoustic wave.

$$P = \Gamma \cdot \mu \cdot \Phi \qquad \text{Equation (1)}$$

Symbol Γ represents the Grüneisen parameter that is an elastic property value obtained by dividing the product of a volumetric expansion coefficient (β) and the square of the speed of sound (c) by specific heat (Cp). Symbol μ is an absorption coefficient of the light absorbing member and is assumed to be the light absorption coefficient of the central wavelength of the irradiated pulsed light 106. Symbol Φ is the light quantity (the quantity of light irradiated to the light absorbing member) at a local area and is a function having a distribution on the xy flat surface. When the absorption coefficient distribution of the light absorbing member inside the irradiation area 203 is an absorption coefficient distribution that is an inverse number of the in-plane distribution Φ of the light quantity, the intensity fluctuation of the light quantity can be cancelled out and a transmitted ultrasonic wave having a uniform sound pressure can be generated. The light absorbing member 111 illustrated in FIG. 2 has an inverse Gaussian-shaped absorption coefficient distribution. The absorption coefficient distribution can be obtained by, for example, controlling the density of the coated ink with an ink jet printer and the like. Note that while it may be difficult to have the absorption coefficient distribution of the light absorbing member be an accurate inverse function of Φ, or to relatively position the light absorbing member and the light source (the light irradiation portion 105) with respect to each other in an accurate manner, in the present exemplary embodiment, it is only sufficient that the distribution of the sound pressure of the transmitted ultrasonic wave becomes close to uniform. It is only sufficient that the intensity fluctuation is less in the intensity distribution of the generated sound pressure of the transmitted ultrasonic wave irradiation area than in the in-plane distribution Φ of the light quantity. Note that a standard deviation may be used as the basis of evaluating the intensity fluctuation. The variation of the intensity of the sound pressure is preferably 10% or under (the minimum value and the maximum value falls within the range of 0.9 times or more to 1.1 times or under with respect to a certain value).

Note that the area of the film 202 other than the area of the light absorbing member is desirably a reflective member. As is the case of the Gaussian-shaped beam, in a case in which the in-plane distribution Φ with a light quantity in which the peripheral light intensity is low is used, a sufficient transmitted ultrasonic wave cannot be generated with the peripheral light quantity. Accordingly, the transmitted ultrasonic wave generated in the periphery cannot be used in the reconstruction and becomes a noise. By providing the reflective member around the light absorbing member, the peripheral light irradiated to the reflective member generates almost no ultrasonic wave; accordingly, noise can be reduced. The material of the film 202 may have a reflection characteristic or a reflective film may be coated thereon, and it is desirable that the material used is a material with a low absorption coefficient that almost does not generate a photoacoustic wave. Specifically, the absorption coefficient is preferably 0.001/mm or under. Note that in a case in which the film itself has a reflection characteristic, the light absorbing member disposed in the film is disposed so as to be on the light irradiating portion 105 side. Furthermore, such a reflective film may be coated so that a transmitted ultrasonic wave is generated in an area that is smaller than the irradiation area, such that a transmitted ultrasonic wave with a certain amount of intensity is obtained.

Note that in a case in which the film 202 is a transparent film, a portion of the pulsed light transmitted to the subject side is absorbed by the subject and the like, becomes a photoacoustic wave, and becomes a noise source. Herein, the reflective film is coated such that the range of the transmitted ultrasonic wave generating area is smaller than the beam irradiation area 203. For example, when the diameter of the beam is 50 mm, the transmitted ultrasonic wave generating area is to be an area of 40 mm.

Incidentally, since the transmitted ultrasonic wave can be transmitted without propagating through the ultrasonic wave generating member 104, it is more suitable that the ultrasonic wave generating member 104 is disposed so that the surface having the light absorbing member is on the subject side. Furthermore, in the present disclosure, since there is a degree of freedom in disposing the drive mechanism 110, the ultrasonic wave generating member 104 is disposed above the probe unit 101. However, the configuration in which the ultrasonic wave generating member 104 is disposed at the bottom portion of the hemispherical probe unit 101 is more desirable since the ultrasonic wave generating member 104 do not interfere with the sound ray of the reflected wave of the subject received by the transducers 102. Note that the ultrasonic wave generating member 104 may be configured of a plurality of sheet members. For example, a sheet member that supports the light absorbing member and a sheet member that has a property of reflecting the pulsed light may be configured to overlap each other or sheet members in which the light absorbing bodies are disposed in different areas may be configured to overlap each other.

In other words, the ultrasonic wave generating member 104 shows a distribution of the light absorption characteristics that compensates the illuminance distribution from the light irradiating portion 105. Furthermore, such a distribution of the light absorption characteristics desirably has, in a planar direction (xy flat surface) of the ultrasonic wave generating member 104, a negative correlation with the illuminance distribution of the pulsed light 106. Furthermore, the light absorbing member 111 is included in the ultrasonic wave generating member 104 with a concentration distribution making the sound pressure intensity distribution smaller than the intensity distribution of the pulsed light 106.

Subject Holding Member

The subject holding member 107 is a member that holds the subject, and in the present exemplary embodiment, the subject holding member 107 is an arc-shaped member disposed in an opening of an apparatus housing. Furthermore, the subject holding member 107 is supported by a support member 112.

In the present exemplary embodiment, measurement of the photoacoustic wave is also performed. Accordingly, since the light irradiated to the subject is transmitted, the subject holding member 107 is, desirably, a member having a high optical transmittance. Furthermore, since the photoacoustic wave and the reflected wave arriving from the subject are transmitted, desirably, a material that has an acoustic impedance that is close to that of the subject is used. Furthermore, rigidity is required since the subject holding member 107 holds the subject. For example, polyethylene terephthalate, polymethylpentene, and polyethylene are included in the examples of such a material. Note that in a case in which measurement of the photoacoustic wave is not performed, the optical transmittance of the holding member 107 is not an issue. Furthermore, while the subject holding member 107 has a function of holding the subject, while measurement is conducted, to reduce the vibration and deformation of the subject, and a function of protecting the probe unit 101 from the subject, if the above functions are not needed, the subject holding member 107 is not needed.

Light Source

The light source 103 is a device that generates the pulsed light 106 irradiated to the subject ultrasonic wave generating member 104. Furthermore, the light source 103 generates the pulsed light 106 irradiated to the subject when the photoacoustic wave is measured.

In order to obtain a large output, the light source 103 is, desirably, a laser light source; however, a light emitting diode or a flashlamp may be used instead. In a case in which a laser is used as the light source 103, a variety of lasers, such as a solid-state laser, a gas laser, a dye laser, and a semiconductor laser can be used. The irradiation timing, the waveform, the intensity, and the like are controlled with the apparatus control unit 109. A light source controller integral with the light source 103 may perform the control instead of the apparatus control unit 109.

The wavelength of the pulsed light 106 is a wavelength that is absorbed by the light absorbing member 111 of the ultrasonic wave generating member 104. Furthermore, as in the present exemplary embodiment, in a case in which measurement of the photoacoustic wave is performed, desirably, the wavelength of the pulsed light 106 is a specific wavelength absorbed by a specific component among the components constituting the subject and is a wavelength enabling the light to propagate to the inside of the subject. Specifically, in a case in which the subject is an organism, the wavelength is preferably 700 nm or higher to 1100 nm or lower. Furthermore, in order to effectively generate the ultrasonic wave or the photoacoustic wave, the light is irradiated for a sufficiently short time period according to the thermal characteristic of the ultrasonic wave generating member or the subject. In a case in which the subject is an organism, in order to effectively generate the photoacoustic wave, the pulse width of the pulsed light generated from the light source 103 is, suitably, about 10 nanoseconds to about 50 nanoseconds. Furthermore, the pulse width for effectively generating the transmitted ultrasonic wave depends on the material of the ultrasonic wave generating member; accordingly, the pulse width may be appropriately configured according to the material of the ultrasonic wave generating member. In order to effectively generate the sonic wave for transmission and the photoacoustic wave with a single light source, the material of the ultrasonic wave generating member is, desirably, a material that allows a pulse width to be used that is similar to the pulse width of the pulsed light irradiated to the subject.

In the present exemplary embodiment, a titanium sapphire laser that is a solid-state laser is used and the wavelength is 760 nm and 800 nm. Note that the pulsed light generated by the light source 103 is irradiated to the subject from the light irradiating portion 105 through an optical transmission line including optical members, such as a lens or a mirror, a diffusing plate, and an optical fiber. Note that in a case in which the distance between the light source and the light irradiating portion is close, the optical transmission line may not include an optical member. Furthermore, a light irradiating portion of the light source may be disposed so as to coincide with an inner wall of the probe unit or on the inner side of the inner wall, and the pulsed light may be irradiated to the ultrasonic wave generating member or the subject without passing through the optical transmission line. In such a case, the light irradiating portion coincides with the light irradiating portion of the light source.

Apparatus Control Unit

The apparatus control unit 109 controls each of the components included in the subject information acquisition apparatus. For example, the apparatus control unit 109 controls the light source, the XY stage, the reception of the transducers, the relative positioning between the ultrasonic wave generating member and the light irradiating portion. Furthermore, the apparatus control unit 109 is an image generation member that acquires information related to the optical characteristic and the acoustic characteristic of the inside of the subject by performing image reconstruction and the like on the basis of the electric signals acquired by the transducers 102.

Typically, the apparatus control unit 109 is a workstation including an independent CPU, a main storage device, and an auxiliary storage device, and the process described above is performed with software stored in advance. The apparatus control unit 109 may be exclusively designed hardware or may be hardware shared with other members. Furthermore, a program that realizes each function may be fed to the system or the apparatus through a network or various computer readable storage mediums, and one or more processor in a computer of the apparatus may readout and execute the program. Furthermore, each function may be realized with a circuit (an FPGA or an ASIC, for example).

Incidentally, the apparatus control unit 109 is capable of acquiring information input by a user of the apparatus and presenting information to the user. Specifically, on the basis of the command input by the user, for example, measurement parameter is changed, the measurement is started and ended, a processing method of the image is selected, patient information and image are saved, and data is analyzed. The above is performed with, for example, a combination of an image display device, such as a display, and an input unit, such as a key board, or a component, such as a touch panel display, in which the image display device and the input unit are integrated.

Method of Reconstructing Image

Processes for reconstructing an image using the acquired photoacoustic wave signal and ultrasonic wave signal will be described next. The reconstruction of an image is performed by the apparatus control unit 109.

A process of acquiring information related to the optical characteristic of the inside of the subject on the basis of the photoacoustic wave signal will be described first. A back-projection algorithm in a three-dimensional space can be applied in such a process. For example, in a case of a universal back-projection (UBP) algorithm, an initial sound pressure distribution p(r) can be obtained with the following Equation (2).

$$P(r) = \int_{\Omega_0} b(r_0, t = |r - r_0|) \frac{d\Omega_0}{\Omega_0} \qquad \text{Equation (2)}$$

A term b $(r_0, t)$ corresponding to projection data in the above is expressed by Expression (3), where $p_d$ $(r_0)$ is the photoacoustic wave signal detected by the detecting element, $r_0$ is the position of each detecting element, t is time, and $\Omega_0$ is the solid angle of the transducers.

$$b(r_0, t) = 2p_d(r_0, t) - 2t \frac{\partial p_d(r_0, t)}{\partial t} \qquad \text{Equation (3)}$$

A similar back-projection algorithm can be used in the reconstruction of the reflected wave. Considering the time taken by the transmitted ultrasonic wave to arrive inside the subject, t is substituted by t' expressed by Equation (4), where $r_s$ is the position of the ultrasonic wave generating member 104, which is an intersecting point when a normal line is extended to the ultrasonic wave generating member 104 from a reconstruction position r. Furthermore, c is the speed of sound. Naturally, in a case in which the speed of sound is greatly different between the subject and the acoustic matching liquid 41, correction considering the difference is performed.

$$t' = t - \frac{r - r_s}{c} \qquad \text{Equation (4)}$$

Incidentally, in a case in which photoacoustic measurement is performed, a portion of the energy of the light that has propagated inside the organism is absorbed by a light absorbing member, such as blood, and an acoustic wave is generated from the light absorbing member upon thermal expansion. Furthermore, in a case in which there is a cancer in the organism, the light is absorbed in a similar manner by the newborn blood vessel of the cancer and a photoacoustic wave is generate. As a result, by performing image reconstruction on the received photoacoustic wave, positional information of the blood vessel and the cancer can be obtained. Furthermore, information, such as oxygen saturation and the like, can be obtained by using the difference, in each substance, in the rate of absorption of the wavelength of the light.

Meanwhile, in a case of reconstruction of the reflected wave, a reflected wave, which is generated by the energy of the transmitted ultrasonic wave propagating inside the organism, reflected and scattered at an interface between substances having different acoustic impedances, such as the boundary surface between a normal site and a tumor, is received. Furthermore, on the basis of the received reflected wave, structural information related to the acoustic characteristic inside the subject can be obtained. As a result, for example, structural information of a boundary surface of a cancer can be obtained.

Note that in an ultrasonic apparatus using a linear probe and the like, for example, ultrasonic waves are transmitted to an object to be examined from ultrasonic wave transducers of 128 elements, and the ultrasonic waves reflected inside the object to be examined are received. While such an ultrasonic apparatus can capture a large structure, such as a tumor interface, it is difficult to capture a small structure, such as calcification. The above is because while in a case of a large interface, the ultrasonic waves return to the ultrasonic wave transducers after being reflected in a specular manner, in a case of a small structure, the ultrasonic waves are scattered to various angles and the amount returning to the ultrasonic wave transducers is decreased. In the present system, the transducers 102 are disposed in the probe unit 101. As a result, the transducers 102 are capable of receiving signals of various angles. In other words, in the present apparatus, even ultrasonic waves that have been scattered by the calcification inside the breast can be received by a number of transducers 102.

Process Flowchart

Figure 3:
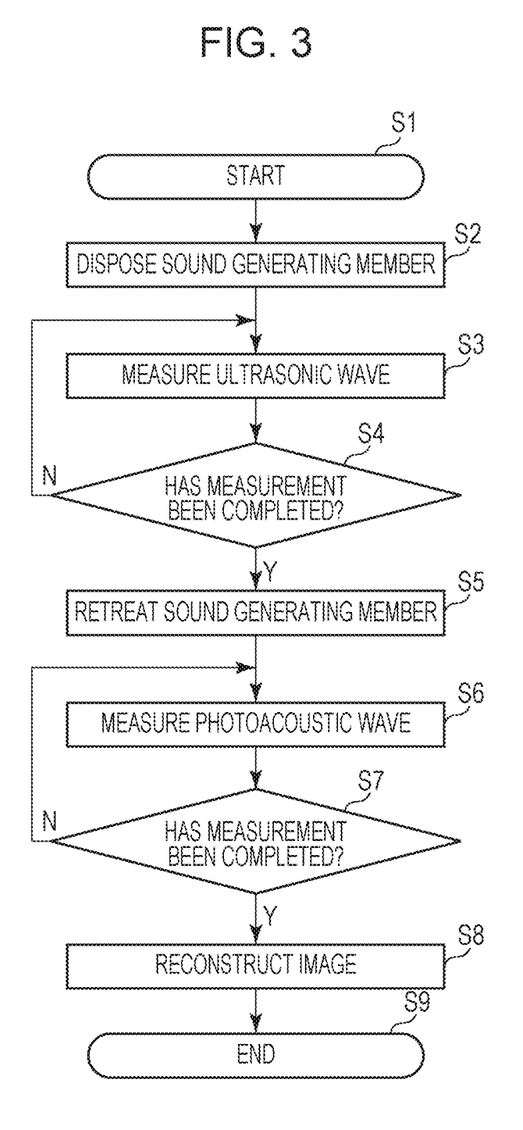
FIG. 3 is a flowchart for conducting measurements according to the exemplary embodiment.

Referring to FIG. 3, a process flowchart of the ultrasonic wave measurement and the photoacoustic wave measurement performed by the subject information acquisition apparatus according to the present exemplary embodiment will be described. Herein, a case in which a breast of an examinee, the breast serving as a subject, is measured will be described.

In step S1, the measurement is started. In such a state, the examinee inserts the breast so that the breast comes into contact with the holding member 107. Furthermore, water serving as an acoustic matching liquid 41 is filled between the holding member 107 and the breast so that no air enters therebetween. Subsequently, when preparation for the measurement is finished, the user operates the apparatus to start conducting the measurement.

In step S2, the ultrasonic wave generating member 104 is disposed at a desired position. In disposing the ultrasonic wave generating member 104, the drive mechanism 110 is used to make adjustments so that the center of the light irradiation area and the center of the in-plane distribution of the optical characteristic of the ultrasonic wave generating member 104 coincide each other.

In step S3, the ultrasonic wave measurement is conducted. In measuring the ultrasonic wave, since the probe unit 101 and the ultrasonic wave generating member 104 move in an integral manner, the relative position between the ultrasonic wave generating member 104 and the intensity distribution of the light irradiated to the ultrasonic wave generating member is fixed. Each time the irradiation light is irradiated to the ultrasonic wave generating member 104, a transmitted ultrasonic wave is generated and reaches the subject. Furthermore, the reflected waves that have been reflected and scattered from the subject are received by the transducers 102. Note that the wavelength of the irradiation light may be a wavelength for conducting photoacoustic measurement, or may be an exclusive wavelength for generating the transmitted ultrasonic wave.

In step S4, confirmation whether the conduction of the intended measurement has been completed is made. If not completed, the process returns to step S3 and the measurement of the ultrasonic wave is conducted. After completing the conduction of the intended measurement, the process proceeds to step S5.

In step S5, since the photoacoustic measurement is conducted, the ultrasonic wave generating member 104 is retreated from the light irradiation area.

In step S6, the photoacoustic measurement is conducted. The photoacoustic measurement is conducted while the position where the subject is irradiated by light is moved with the XY stage, so as to obtain an image with a wide area. Herein, in order to calculate oxygen saturation, lights having two wavelengths, that is, 760 nm and 800 nm, are irradiated alternately at the same position.

In step S7, confirmation whether the conduction of the intended measurement has been completed is made. If not completed, the process returns to step S6 and the photoacoustic measurement is conducted. After completing the conduction of the intended measurement, the process proceeds to step S8.

In step S8, the image reconstruction is performed. In reconstructing the image, image reconstruction of the ultrasonic wave and photoacoustic image reconstruction are performed. As required, the ultrasound image and the photoacoustic image may be fused by image processing.

In step S9, the measurement is ended. The acquired image is checked and if the acquired image is a desired image, the measurement is ended. Naturally, when conducting a measurement of the opposite breast, the measurement may be continued by returning to step S1. Note that the ultrasonic wave measurement and the photoacoustic measurement may each be conducted based on independent flowcharts.

By having the above configuration, the intensity distribution of the generated transmitted ultrasonic wave can be changed. As a result, a desired ultrasound image can be acquired even in an apparatus that measures the photoacoustic wave image and the ultrasound image with the same probe unit.

Other Variation Example

In the exemplary embodiment described above, since the ultrasonic wave generating member 104 has a substantially flat surface, the transmitted ultrasonic wave generating area also has a substantially flat surface; however, the ultrasonic wave generating member 104 and the transmitted ultrasonic wave generating area may each have a curvature as illustrated in FIG. 4B. For example, a curvature is formed such that the transmitted ultrasonic wave generated in the ultrasonic wave generating member 104 forms a focus point at a point 20 mm from the surface of the subject. With the above, the transmitted ultrasonic wave can be concentrated to the area in the subject where the measurement is intended.

Furthermore, in the exemplary embodiment described above, the ultrasonic wave generating member 104 has an absorption coefficient distribution that generates an ultrasonic wave having an intensity distribution (having an intensity close to uniform) in which an intensity fluctuation is smaller than the intensity fluctuation of the irradiation light. However, the absorption coefficient distribution is not limited to the above form and the ultrasonic wave generating member 104 may have an absorption coefficient distribution in which the intensity change of the in-plane ultrasonic wave is large.

Figure 4C:
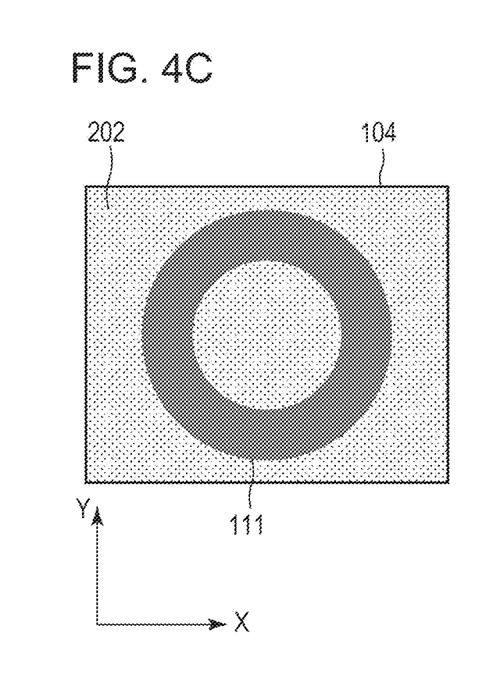

FIG. 4C illustrates an example of the ultrasonic wave generating member 104 in which a ring-shaped light absorbing member 111 is disposed. In the ultrasonic wave generating member 104, for example, a light absorbing member 111 having a uniform absorption coefficient is disposed, for example, in an area having an inside diameter of 30 mm and an outside diameter of 50 mm. In such a case, since the absorption coefficients of the light absorbing member 111 and the film 202 are different, the irradiation area of the ultrasonic wave generating member has a ring-shaped absorption coefficient distribution. Since the specular reflection reflected from the interface is formed into an image, in the ultrasound image obtained by generating a planar ultrasonic wave having a substantially uniform intensity to the subject, it is difficult to capture scatters caused by minute calcifications. However, by using the ultrasonic wave generating member having such a ring-shaped light absorbing member, a photograph like a dark field photograph can be taken such that imaging can facilitated even with a scattered and weak ultrasonic wave.

Furthermore, the ultrasonic wave generating member 104 may be used to define the irradiation area of the photoacoustic wave measurement. In the case of the exemplary embodiment described above, the ultrasonic wave generating member is retreated from the optical path between the ultrasonic wave measurement and the photoacoustic wave measurement; however, by not retreating the ultrasonic wave generating member and by performing the photoacoustic wave measurement, emission of light to a portion of the subject can be prevented. Furthermore, in order to obtain an optional light intensity, the in-plane distribution of the transmittance may be adjusted. In such a case, an ultrasonic wave generating member 104 having an absorption coefficient distribution suitable for the transmitted ultrasonic wave, and an ultrasonic wave generating member 104 having an absorption coefficient suitable for the photoacoustic wave measurement may be prepared and may be used after being replaced with the drive mechanism 110. By so doing, the desired ultrasonic wave measurement and photoacoustic measurement can be conducted. Note that the ultrasonic wave generating member used during the photoacoustic wave measurement may be a member formed of an area with a low (high in transmittance) light absorption coefficient and an area with a high reflectance, and may be a member that hardly generates the ultrasonic wave.

Furthermore, in the ultrasonic apparatus of the exemplary embodiment described above, while the ultrasonic wave measurement and the photoacoustic wave measurement are both conducted, the present disclosure can be applied to any ultrasonic apparatus that generates a planar ultrasonic wave, and, for example, can be applied to an ultrasonic apparatus that does not conduct a photoacoustic wave measurement and only conducts an ultrasonic wave measurement.

Furthermore, although the ultrasonic apparatus of the exemplary embodiment described above includes an arcuate subject holding member 107, the shape of the subject holding member is not limited to the above shape. Furthermore, the present disclosure can be applied to an ultrasonic apparatus that does not include a subject holding member.

The preferable exemplary embodiment and the variation example of the present disclosure have been described above; however, the present disclosure is not limited to the exemplary embodiment and the variation example, and various modifications and changes can be made within the gist of the disclosure.

The present disclosure is capable of, in a photoacoustic induced ultrasonic imaging apparatus, providing an ultrasonic apparatus that is capable of generating an ultrasonic wave having a desired intensity distribution, or that is capable of making the intensity distribution of the generated ultrasonic wave close to a desired intensity distribution.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-016445 filed Jan. 29, 2016, which is hereby incorporated by reference herein in its entirety.

What is claimed is:

1. An ultrasonic apparatus comprising:
a transducer configured to receive an ultrasound and convert the ultrasound into an electric signal;
a planar ultrasound generating member acoustically coupled to the transducer via an acoustic matching liquid and showing a planar distribution of an optical absorption property; and
a light emitting portion acoustically coupled to the planar ultrasound generating member via the acoustic matching liquid and configured to emit a pulsed light and form a planar illuminance distribution on the planar ultrasound generating member;
wherein the planar distribution of the optical absorption property and the planar illuminance distribution have a negative correlation with respect to each other.

2. The ultrasonic apparatus according to claim 1, wherein the planar ultrasound generating member shows the planar distribution of the optical absorption property configured to compensate the planar illuminance distribution.

3. The ultrasonic apparatus according to claim 1, wherein the ultrasound generating member includes a light absorbing member showing the planar distribution of the optical absorption property so as to form a planar intensity distribution of the sound pressure smaller than the planar illuminance distribution.

4. The ultrasonic apparatus according to claim 1, further comprising a moving unit configured to change a relative position between an optical path of the pulsed light from the light emitting portion and the planar ultrasound generating member.

5. The ultrasonic apparatus according to claim 1, wherein the planar ultrasonic generating member generates an ultrasound that has a planar intensity distribution of a sound pressure smaller than the planar illuminance distribution.

6. The ultrasonic apparatus according to claim 1, wherein the optical reflective member and the planar ultrasound generating member are disposed on a sheet member disposed between the light emitting portion and the subject.

7. The ultrasonic apparatus according to claim 1, wherein the optical reflective member masks a peripheral of an irradiation area.

8. The ultrasonic apparatus according to claim 6, wherein the light emitted from the light emitting portion is irradiated to the planar ultrasound generating member and the optical reflective member.

9. The ultrasonic apparatus according to claim 4, wherein the absorption coefficient distribution of the planar ultrasound generating member is ring-shaped.

10. The ultrasonic apparatus according to claim 1, wherein the planar ultrasound generating member includes a plurality of sheet members.

11. The ultrasonic apparatus according to claim 1, wherein the planar distribution of the optical absorption property is inversely correlated with the planar illuminance distribution.

12. An ultrasonic apparatus comprising:
a transducer configured to receive an ultrasound and convert the ultrasound into an electric signal;
a planar ultrasound generating member showing a planar distribution of an optical absorption property; and
a light emitting portion configured to form a planar illuminance distribution on the planar ultrasound generating member;
wherein the planar distribution of the optical absorption property is inversely correlated with the planar illuminance distribution.

13. The ultrasonic apparatus according to claim 12, wherein the planar distribution of the optical absorption property compensates the illuminance distribution.

14. The ultrasonic apparatus according to claim 12, wherein the planar ultrasound generating member generates an ultrasound that has a planar intensity distribution of a sound pressure smaller than the illuminance distribution.

15. The ultrasonic apparatus according to claim 1, further comprising
an optical reflective member disposed at a peripheral region of the planar ultrasound generating member and configured to reflect a part of the light from the light emitting portion.

16. The ultrasonic apparatus according to claim 15,
wherein the optical reflective member reduces a noise from the peripheral region of the planar ultrasound generating member.

17. The ultrasonic apparatus according to claim 15,
wherein the optical reflective member reduces a photoacoustic wave from the peripheral region of the planar ultrasound generating member.

18. The ultrasonic apparatus according to claim 12,
wherein the planar ultrasound generating member is acoustically coupled to the transducer via acoustic matching liquid and the light emitting portion is acoustically coupled to the planar ultrasound generating member via the acoustic matching liquid.

* * * * *